United States Patent
Sahai et al.

(10) Patent No.: US 10,321,888 B2
(45) Date of Patent: Jun. 18, 2019

(54) WIRELESS STETHOBROADCASTING INSTRUMENT FOR MEDICAL TRAINING

(71) Applicants: Nikhil Sahai, Webster City, IA (US); Subhash Sahai, Jr., Webster City, IA (US); Arun Somani, Ames, IA (US); Koray Celik, Cedar Rapids, IA (US)

(72) Inventors: Nikhil Sahai, Webster City, IA (US); Subhash Sahai, Jr., Webster City, IA (US); Arun Somani, Ames, IA (US); Koray Celik, Cedar Rapids, IA (US)

(*) Notice: Subject to any disclaimer, the term of this patent is extended or adjusted under 35 U.S.C. 154(b) by 106 days.

(21) Appl. No.: 14/853,211

(22) Filed: Sep. 14, 2015

(65) Prior Publication Data

US 2016/0078779 A1    Mar. 17, 2016

Related U.S. Application Data

(60) Provisional application No. 62/049,704, filed on Sep. 12, 2014.

(51) Int. Cl.
  *G09B 23/28* (2006.01)
  *A61B 7/02* (2006.01)

(52) U.S. Cl.
  CPC ............ *A61B 7/02* (2013.01); *G09B 23/28* (2013.01)

(58) Field of Classification Search
  CPC ............ G09B 23/28; A61B 7/02; A61B 7/04
  See application file for complete search history.

(56) References Cited

U.S. PATENT DOCUMENTS

| | | | |
|---|---|---|---|
| 5,774,563 A | 6/1998 | DesLauriers et al. | |
| 5,825,895 A * | 10/1998 | Grasfield | A61B 7/04 381/67 |
| 5,888,187 A * | 3/1999 | Jaeger | A61B 5/0031 600/23 |
| 6,139,505 A | 10/2000 | Murphy | |
| 6,498,854 B1 * | 12/2002 | Smith | A61B 7/04 381/67 |
| 7,115,102 B2 * | 10/2006 | Abbruscato | A61B 7/045 128/904 |
| 8,491,488 B1 | 7/2013 | Criley et al. | |
| 2004/0068194 A1 * | 4/2004 | Johnson | A61B 5/0002 600/508 |
| 2004/0076303 A1 | 4/2004 | Vyshedskly et al. | |
| 2007/0178430 A1 * | 8/2007 | Lecat | G09B 23/28 434/266 |

(Continued)

*Primary Examiner* — Peter R Egloff
(74) *Attorney, Agent, or Firm* — McKee, Voorhees & Sease, PLC

(57) ABSTRACT

A method and system provides improved auscultation training for medical students and other healthcare providers. The system includes an instructor stethoscope which generates an acoustic output corresponding to an ausculatory sound from the patient. The acoustic output is wirelessly transmitted to earpieces worn by one or more students such that the students can simultaneously listen with the instructor to the ausculatory sound. The acoustic output may be recorded for future listening and training. The instructor stethoscope includes a resonance chamber having a capacitive pickup to receive the ausculatory sound wave from the stethoscope chest piece. The acoustic wave is converted to an analog signal and then to a digital signal, which is broadcast and then re-converted to an analog signal for the listening students.

19 Claims, 2 Drawing Sheets

(56) References Cited

U.S. PATENT DOCUMENTS

| | | | |
|---|---|---|---|
| 2007/0273504 A1 | 11/2007 | Tran | |
| 2008/0298603 A1 | 12/2008 | Smith | |
| 2009/0305212 A1* | 12/2009 | McKenzie | G06F 19/3437 |
| | | | 434/266 |
| 2010/0056956 A1* | 3/2010 | Dufresne | A61B 7/04 |
| | | | 600/586 |
| 2011/0038497 A1* | 2/2011 | Chae | H04R 19/04 |
| | | | 381/312 |
| 2012/0310115 A1* | 12/2012 | Bedingham | A61B 7/04 |
| | | | 600/586 |
| 2015/0190110 A1* | 7/2015 | Chong | H04R 1/46 |
| | | | 600/528 |
| 2015/0201272 A1 | 7/2015 | Wong | |

* cited by examiner

WIRELESS STETHOBROADCASTING INSTRUMENT FOR MEDICAL TRAINING

FIELD OF THE INVENTION

The field of the invention is effective mediate auscultation training for medical students. In particular, a device and method adapted for such training are disclosed.

BACKGROUND OF THE INVENTION

The field of the invention is effective mediate auscultation training for medical students.

The modern stethoscope is an acoustic medical device that transmits auscultatory sounds from a patient's internal organs to human ear in an air coupled manner. A flexible membrane strung over an airtight metallic bell by means of a pressure sensitive tuning mechanism which (without the vibration of the instrument itself) adds considerably to the sound. The traditional way of auscultation using a stethoscope is to press it against the skin of a patient in a very precise manner.

The proper technique to hold the instrument is key to accurate auscultation, and such technique is considered an art as well as science. Coupled with the proper location of the auscultation (pulmonary, aortic, suprasternal, tricuspid, mitral, pulmonary, or apex) the angle at which the device is held, and the pressure at which it is applied to the patient, create different airflow and dynamically modify certain properties of the instrument. This in turn causes its air column to amplify different resonant frequencies. As a result, the instrument is said to be "tuned" to different acoustic waveforms, belonging to different organs or systems.

Auscultation is spatio-temporally variant phenomena. For example the heart follows midsystolic, holosystolic (or pansystolic), early, mid and late diastolic patterns. The speed and intensity changes with the patient's condition, as well as metabolism at the time measurement was taken. The different sounds of these cycles may radiate toward cartoid arteries, apex, precordium, axilla, sternum, or none at all. The medical quality of the auscultation may be described as rumbling, blowing, harsh, rough, high-pitch, medium-pitch, low-pitch, and these may or may not be accompanied by thrill (vibrato caused by turbulent blood flow). Each of these parameters may have any of the six medically accepted intensity grades:

1. Barely audible, even to the trained ear.
2. Easily audible.
3. Equal to normal heart sound intensity.
4. Loud with palpable thrill.
5. Audible when stethoscope is in partial contact with the chest, and murmur has a palpable thrill.
6. Audible when stethoscope is over but not touching the chest, and murmur has palpable thrill.

These qualities are of dramatic importance to a successful diagnosis. For example, a tricuspid auscultation (requires turning the chestpiece over to diaphragm side and use firm pressure) radiating towards precordium with harsh quality and high pitch may indicate the patient has a ventricular septal defect. A blowing quality instead of harsh, all else being equal, suggests the patient instead has a tricuspid insufficiency. These two different conditions produce sounds that are difficult to distinguish, even for a trained ear. The intensity grade of the auscultation can make this distinction even more difficult. Improper handling of the stethoscope over the measurement site also makes the distinction difficult. These difficulties create a risk that students might learn the incorrect sounds and associate them with wrong diagnoses.

The character of an auscultation as perceived by the human ear is controlled by the four distinct properties: pitch, loudness, timbre, and duration (time between two adjacent periods of zero loudness). Timbre is the sonic quality of a sound that defines the distinct character. For example, assume a piano, then a cello, play the same note with exactly the same loudness, duration, and pitch bend. Humans can still tell which sound came from which instrument due to the timbre. Timbre is noise invariant, and human hearing is incredibly sensitive to timbre, probably because timbre is how humans add emotion to speech. However it is dramatically less sensitive to other parameters of sound (where noise is propagated), and this sensitivity varies according to a Fletcher-Munson curve. Noise occurs principally in the pitch domain; it is a cacophony of pitched components which could end up drowning the timbre.

Loudness is how an individual perceives the volume of a sound at a certain sound pressure level. The difference between the softest and the loudest perceivable volume levels is named the dynamic range of the ear. The point where the volume is so low that the ear ceases to hear the sound is named the threshold of audibility which differs for person to person and for different pitches. In general the threshold for the higher pitches is raised when a person is getting older, until finally deafness for this pitch range occurs. Further, when the volume level is either too low or too loud for an extended period of time (such as in auscultation training sessions) more concentration is needed and the person's hearing will tire after some hours, also changing its sensitivity. It is impossible to adjust a conventional stethoscope to cope with these changes and ensure uniform loudness is heard.

In conventional patient care the experienced physician controls the stethoscope and hears the proper sounds directly. In a research hospital setting with a group of medical students to auscultate on one patient, it is impossible for the training doctor to ensure every student has heard the exact same sound mentioned in the lecture. This is because the students are yet learning how to position and hold the instrument properly. A Stethoscope is extremely sensitive to precise hand-ear coordination, and will either produce the correct sound, or a very wrong sound, or lack thereof. Further, student training requires multiple measurements which is inconvenient for the patient.

In conventional student training, one method for producing or electronic version of auscultation is to use a stethophone having electric microphones inside the ear holes to amplify the sound for play over a speaker system for simultaneous listening by students. This solution is acceptable only for very basic practice because (i) it cannot reproduce the complex low-frequency characteristics of the real instrument, (ii) the output may sound different based on the positioning and capabilities of amplifying unit as well as the shape of the room, (iii) it is prone to positive feedback from the amplifying instrument and to electrical noise from other medical and non-medical devices (e.g. fluorescent lamps), and (iv) it is a violation of patient's privacy rights since the sound is broadcast in a way it can be heard by third parties. The auscultation sounds can also be recorded for later playback to one or more students, which has the same problems. Medical students in auscultation training find themselves in a situation where the sound produced by the patient is not being heard by them at the time, location, and handling which it was produced. Instead it is heard by the experienced doctor, and described to the students verbally, who must learn to locate the same sound.

Sharing a single stethoscope is anatomically impossible since the instrument should form an air pressure barrier with both ears simultaneously lest it will not operate properly. Prior art utilizes dual-earpiece training stethoscopes for joint use by the training doctor and student, such as those sold by 3M, Mabis, and Sprague. The problem with these devices is threefold; (i) they can be used with only one student at a time. (ii), because they divide the sound and require longer tubes (2×40" tubes versus the conventional 1×28"), wave attenuation occurs and the auscultation becomes weaker, resulting in a hearing of incorrect intensity grade. And (iii), more tubes in the way increases the risk of tubes rubbing against each other (especially if the patient is not cooperating such as in the case of children, or the room is small), which will pollute the auscultation.

SUMMARY OF THE INVENTION

The device and method proposed in this invention aims at improving the learning curve for using these instruments in a research hospital or other medical training setting without requiring one measurement per student. The invention involves generating acoustic output directly from one stethoscope instrument at the hands of an experienced training physician (so as to ensure instrument is held properly and auscultation is accurate), and wirelessly broadcasting this sound from the physician's stethoscope to the stethoscopes of many students simultaneously, in a real-time, high-fidelity manner.

The disclosed embodiments take a different approach from the prior art and provides a method based on continuous transformation of the original air coupling mechanism into a secure digital wireless signal, where it is transduced to auscultation back at the earpieces of stethoscopes the students are wearing, where the impulse response function of the acoustic system of the instrument and mathematical model that is used to produce the output signal of the instrument are faithfully retained.

The generality of this method allows for use not only in training hospitals but also in other applications. For example, the auscultation audio can be directed to external recording devices, such as a laptop or MP3 recorder, and the same connection can be used to listen to the previously recorded auscultation through the student stethoscope headphones, allowing for more detailed study for general research, as well as evaluation and consultation regarding a particular patient's condition and telemedicine, or remote diagnosis.

The proposed method combines ideas from the fields of digital signal processing and acoustics. The disclosed invention provides a method for converting an off-the-shelf tunable stethoscope into an effective medical teaching aid. As one example, the very popular 3M™ Littmann® Cardiology III™ stethoscope (henceforth LCIII) was chosen as the host. However, many other popular stethoscopes can be used with the invention, including designs such as the Sprague-Rappaport Stethescope. The LCIII has a double-sided chestpiece featuring a tunable diaphragm for adult and open bell for pediatric auscultation or low frequencies. The chestpiece has a single hose barb meant to be manually inserted into a single tube (featuring parallel sound channels internal to the tube).

The invention is composed of two devices: a student device (SD) and an instructor device (ID). The invention is applied to the LCIII by means of pulling the chestpiece apart from the tube, inserting the chestpiece into the SD or ID, and the tube into the new hose barb supplied by the invention. Once this is performed, all SD units in the room will be able to reproduce the exact acoustic patterns of a single ID unit in a wireless and hoseless manner.

The reproduction at SD is based on dynamic reproduction of the impulse response of the acoustic system of the ID instrument. The method is based on the assumption that a real stethoscope in its acoustic resonator system appears close enough in its characteristics to a corresponding linear acoustic system model, and that the mathematical methods applicable for such linear system produce acceptable results. The proposed method also assumes that the system can be reviewed as time-invariant for time intervals that are short enough.

The invention extends to apparatus comprising:

a hypoallergenic resonation tube leading to a capacitive gold pickup;

a noiseless transducer converting the acoustic wave to an exact analog signal representation of the wave;

a digitizing transducer receiving the analog signal and sampling the current state of the acoustic system of the stethoscope;

a processing block packaging the digital representation of auscultation for secure wireless transmission; and a radio transmission block for broadcast from the ID unit for reception by the SD units.

DETAILED DESCRIPTION OF THE INVENTION

Figure 1:
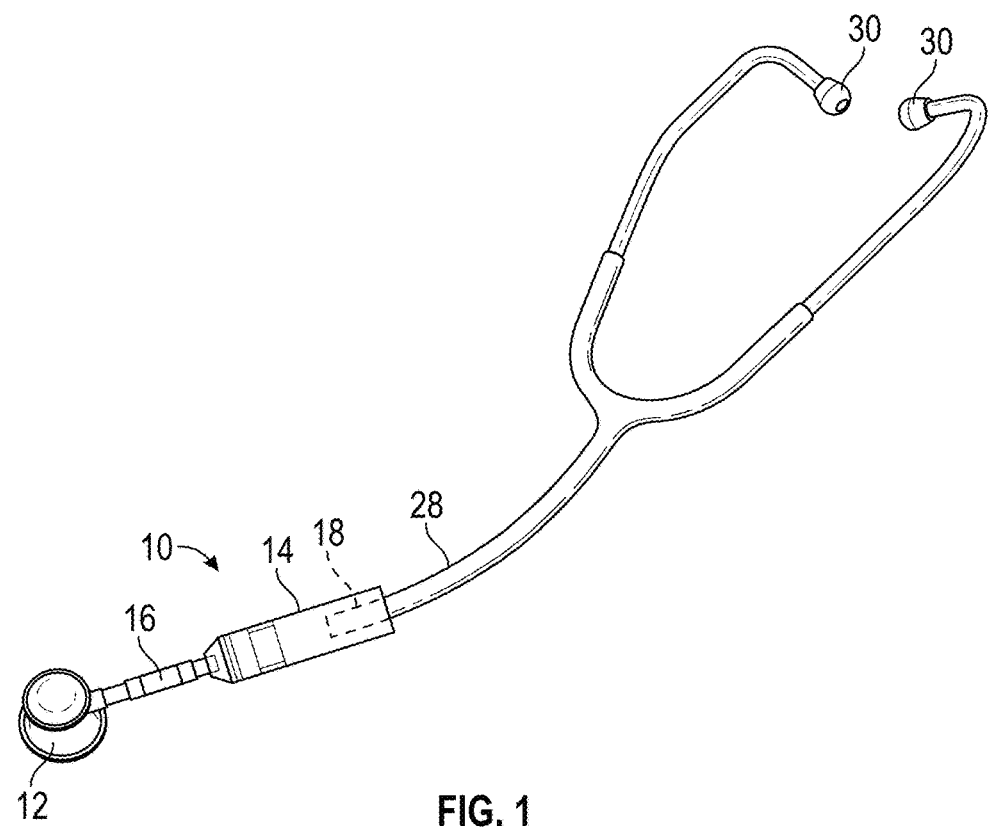
FIG. 1 is a perspective of a generalized instructor's stethoscope.
Figure 2:
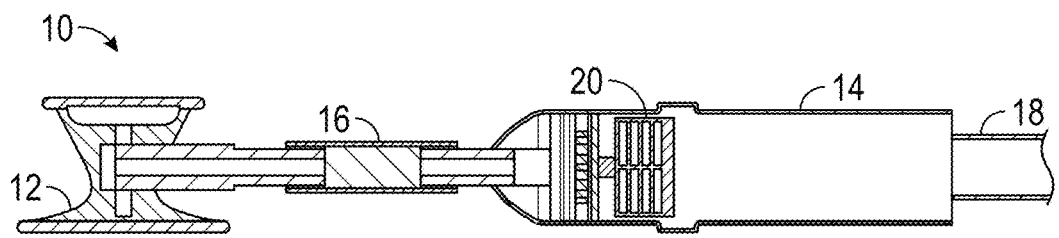
FIG. 2 is a side elevation view of the stethoscope of FIG. 1.
Figure 3:
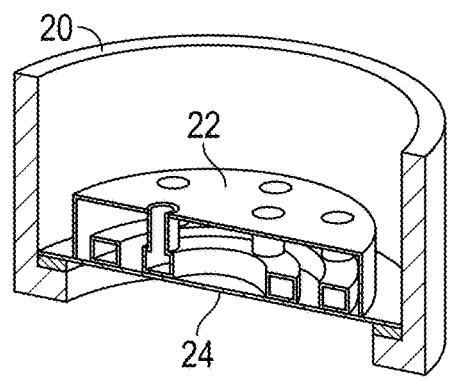
FIG. 3 is a partial sectional view of the electro static capacitor in the instructor stethoscope.
Figure 4:
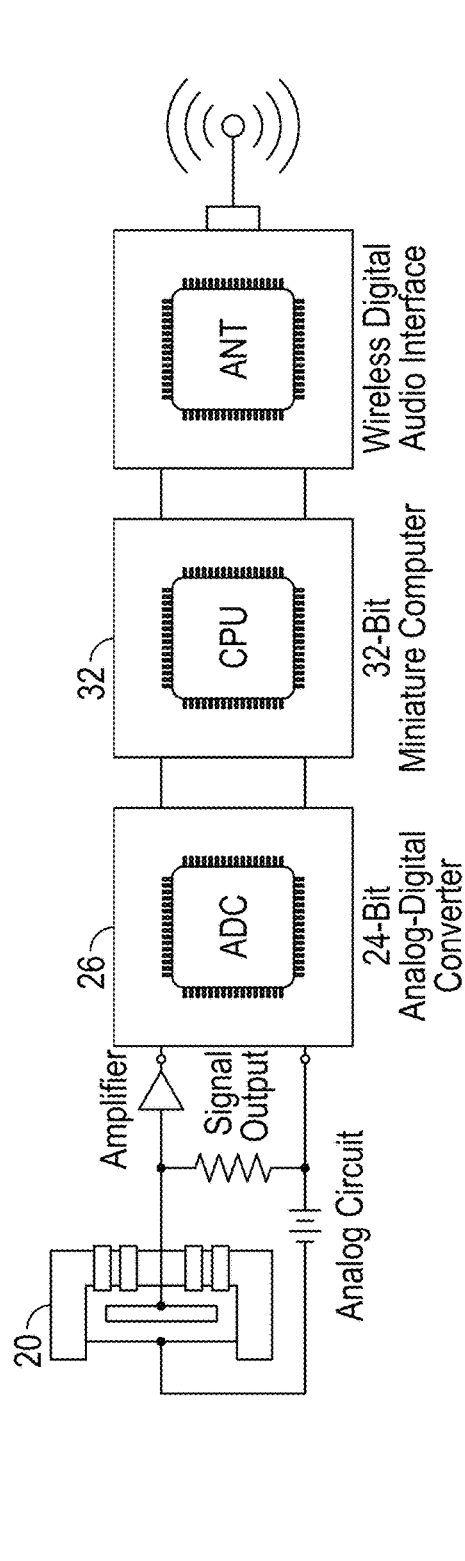
FIG. 4 is schematic of the electro mechanical components for the instructor stethoscope.
Figure 5:
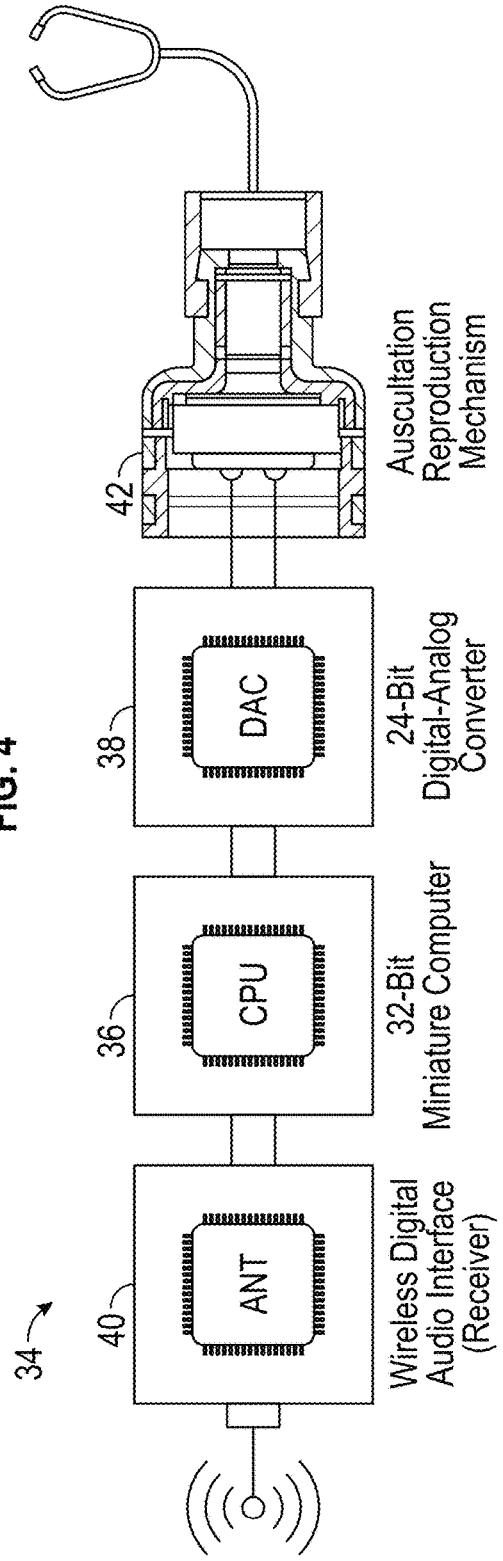
FIG. 5 is schematic of the electro mechanical components for the student stethoscope.

The instructor stethoscope of the present invention is generally designated by the reference numeral 10 in FIGS. 1 and 2. This instructor's device (ID) can be modeled in electrical terms with the exciter-resonator interaction scheme of, where noise propagation channels of sound are electrically synthesized in such a manner mechanical and electronic methods are used to prevent noise from being introduced into the system, and leaving the timbre untouched for the human ear's perception. Such discretization of the patient interaction simplifies the model of the resonator to a linear time-invariant system. This is accomplished by first directing the acoustics from the chestpiece 12 into a tunable stainless steel resonance chamber or tube 14, specially designed to amplify the typical frequency range of auscultation sounds emitted by the human body. The resonance chamber 14 exists only in the ID component of the invention, since students do not have need or control of this part. The instructor can control the resonance chamber amplification by means of manually rotating the tunable adapter 16. The chamber 14 follows a worm screw into the hose barb 18, and therefore rotating the resonation chamber at the time of manufacture alters the length of the chamber, effectively tuning it. Then the length is set and not adjustable for use of the stethoscope.

At the forward end of the resonation chamber 14 there exists an electrostatic capacitor 20 with two gold foil plates 22, 24. One of those plates 22 is electromagnetically suspended in the air and the other 24 is fixed mechanically. This makes the suspended plate 22 incredibly sensitive to air movements. The suspended plate 22 acts as a diaphragm where vibrations induced by changes in air pressure produce changes in the distance between the two plates. The plates 22, 24 are DC biased with a fixed charge (Q, represented in Coulombs) by means of a battery induced DC voltage maintained across the capacitor plates. Vibrations in the air, according to the capacitance equation C=QV, where C is capacitance in farads and V is potential difference in volts, capacitance of the plates is inversely proportional to the distance between them. As the capacitance changes (between 5-100 pF) a bias resistor (100 MΩ or higher) together form an electrical filter that is band-pass for the audio signal, and low-pass for the bias voltage, where time constant of the resulting high-impedance RC circuit equals the product of the resistance and capacitance. Within the time-frame of the capacitance change (about 50 ms at 20 Hz) the charge is practically constant and the voltage across the capacitor 20 changes instantaneously to reflect the change in capacitance. Since gold foil is microscopically thin it represents a very small mass to be moved by the incident sound wave. The wave does not lose energy in the process (the main reason why conventional sound recording is noisy —the wave is expected to do all the physical work). A very high quality representation of the sound is captured in terms of time variant DC voltage.

The frequency band for auscultation is relatively narrow; the majority of sounds such as murmurs, clicks, occur between 5 and 10 Hz. A very small portion of sounds such as thrills may reach as much as 0:1 kHz. Generally speaking, anything above 0:1 kHz heard out of a stethoscope is probably noise (e.g. rubbing against the patient's clothes). Out of all phenomena capable of making sounds internally, there is nothing in human body that moves fast enough to exceed these frequencies. This narrow band must be digitized, and discretized by sampling. The disclosed invention uses a 24-bit analog to digital conversion circuit (ADC) 26 for digitization, and a 96 kHz sample rate for discretization. This means that the voltage on the electrostatic capacitor 20 is measured 96,000 times every second, and the measurement is sensitive to 16,777,216 different voltage values between 0 and 48 volts DC. In other words, air movements as gentle as to cause only a few microvolts of change in the capacitor 20 will be captured. These numbers are far beyond the capabilities of human ear to distinguish sound timbres and volumes, therefore the sound capture quality of the disclosed invention must be satisfactory for medical use. A small gain knob is provided on the ID units for the doctor to amplify a sound if desired.

In this exciter/resonator model where excitation function is the electrostatic capacitor 20 and the resonating body is the resonance tube 28. The sonic energy generated by the patient cannot leak away in the air without first being captured. After the capture, the flow of sonic energy is maintained as a continuous stream since the gold foil moves in such a way it is transparent to the sound wave. Sound passes through the foil, then continues through the resonance chamber 20, over the digitizing circuits, and is mechanically connected directly to the earpieces 30. Therefore in the ID unit 10 the instructing doctor hears the actual conventional stethoscope sound.

The digitized and discretized signal is received by a miniature 32-bit computer 32 with at least 80 MHz clock rate and at least 512 kilobytes of memory. The sound is converted into a stream of data packets, and passed to a host controller interface (HCl) (not shown). This interface handles the protocol stack which defines multiplexing of data, segmentation and reassembly of packets, and the one-way transmission management of multicasting data to a group of other SD devices 34. Each payload contains up to 64 kB of data, transmitted asynchronously by performing retransmissions and CRC checks. Payloads are broadcast into the environment by means of a radio signal. Payloads may be encrypted at the choice of the doctor. The ID device 10 has the capability to broadcast directly to a laptop computer, smart phone, MP3 player, or other mobile device.

The SD units 34 are similar to ID unit 10 except they do not have the electrostatic capacitor 20, nor resonation chamber or tube 14, nor the 24-bit ADC 26. They also have no controls which the student can change. The SD 34 includes a 32-bit miniature computer 36, a 24 bit DAC 38 and a radio receiver 40. The electrostatic capacitor 20 is replaced with an electrostatic transducer 42 and positioned at the opposite end of the student device 34 (earpiece end instead of chestpiece end). The transducer foil in the SD unit 34 vibrates in the exact same pattern as the gold foil in ID unit 10, but without the input from the resonation tube 14, the foil only serves to produce an exact replica of the auscultation for the student, at the control of the instructing doctor. The SD units 34 may be plugged into a laptop computer, smart phone, MP3 player, or other mobile device and record their readings on this device, or may be connected wirelessly.

A software on these devices may serve to record, transmit, and analyze the auscultation for telemedicine, research, and other purposes.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. An auscultation training system for use with an off-the-shelf stethoscope having a chest piece, a hose connected to the chest piece, and an ear piece connected to the hose, the training system comprising:

a resonation chamber inserted between the chest piece and the ear piece after the chest piece and ear piece are pulled apart, such that the resonance chamber connected to the chest piece and to the ear piece forms an instructor device;

the resonation chamber including an internal electrostatic capacitive pickup to receive the sound wave from the chest piece;

a sound converter operatively connected to the resonation chamber to convert a first analog sound wave from the chest piece into a digital signal and a transmitter operatively connected to the sound converter to transmit the digital signal wirelessly;

at least one student device in communication with the instructor stethoscope, and having an ear piece, a receiver to receive the digital signal, and a signal converter to convert the digital signal into a second analog signal in real time representing the sound wave;

whereby an instructor wearing the instructor stethoscope and a student wearing the student device simultaneously hear an identical sound corresponding to the first analog sound wave.

2. The auscultation training system of claim 1 wherein the pickup includes first and second foil plates.

3. The auscultation training system of claim 2 wherein the first foil plate is suspended electromagnetically in air and the second foil plate is fixed to the resonance chamber.

4. The auscultation training system of claim 2 wherein the first plate is electromagnetically suspended in air.

5. The auscultation training system of claim 1 wherein the sound converter includes an analog to digital converter.

6. The auscultation training system of claim 5 wherein the signal converter includes a digital to analog converter.

7. The auscultation training system of claim 1 wherein the pickup includes a pair of gold plates.

8. The auscultation training system of claim 7 wherein one of the gold plates is fixed and the other of the gold plates is suspended.

9. The auscultation training system of claim 1 wherein the chamber is tunable.

10. The auscultation training system of claim 1 wherein the chamber has an adjustable length.

11. The auscultation training system of claim 1 further comprising a computer between the converter and the transmitter to convert the digital signal to a digital waveform.

12. The auscultation training system of claim 1 wherein the sound converter has a capacitor and the signal converter has a transducer.

13. The auscultation training system of claim 1 wherein the sound wave of the instructor stethoscope corresponds to a first analog signal, and the analog signal converted in the student stethoscope matches the first analog signal.

14. A method of auscultation training of students, comprising:
separating a chest piece from an ear piece of an off-the-shelf stethoscope; then
inserting a resonance chamber with an internal electrostatic capacitor between the chest piece and the ear piece;
providing an air tube from the chest piece to the resonance chamber;
providing an air tube from the resonance chamber to the ear piece;
the chest piece, resonance chamber, ear piece, and air tubes forming an instructor stethoscope;
generating a first analog sound wave with the instructor stethoscope worn be an instructor and used on a patient corresponding to an ausculatory sound from the patient's body;
converting the analog sound wave to a digital acoustic output using the instructor stethoscope;
wirelessly transmitting in real time the digital acoustic output to a student stethoscope worn by a student;
converting the digital acoustic output to a second analog sound wave using the student stethoscope for simultaneous listening of the ausculatory sound by the instructor and the student; and
the first and second analog sound waves substantially matching one another.

15. The method of claim 14 wherein the acoustic output is transmitted to a plurality of students each wearing an earpiece such that all the students listen to the ausculatory sound simultaneously with the instructor.

16. The method of claim 14 further comprising recording the acoustic output for listening at a later time.

17. The method of claim 14 wherein the conversion discretizes the first analog signal.

18. The method of claim 14 further comprising boosting the acoustic output before transmitting.

19. A plug-in accessory for an off-the-shelf stethoscope having a chest piece, an ear piece, and a tube interconnecting the chest piece and ear piece, the accessory comprising:
a body having opposite ends adapted to be plugged into the chest piece and into the ear piece after the chest piece and ear piece are separated;
the body being selected from an instructor insert to create an instructor device and a student insert to create a student device;
the instructor insert having a resonation chamber with an internal electrostatic capacitor to convert analog sound wave from the chest piece into a digital signal and a transmitter operatively connected to transmit the digital signal wirelessly; and
the student insert having a receiver to receive the digital signal, and a signal converter to convert the digital signal into an analog signal in real time representing the sound wave.

* * * * *